United States Patent [19]

Simons

[11] 4,266,965
[45] May 12, 1981

[54] 2-(α-NAPHTHOXY)-N,N-DIETHYL PROPIONAMIDE AS AN AQUEOUS FLOWABLE CONCENTRATE

[75] Inventor: Richard W. Simons, Suisun, Calif.

[73] Assignee: Stauffer Chemical Company, Westport, Conn.

[21] Appl. No.: 89,070

[22] Filed: Oct. 29, 1979

[51] Int. Cl.$^3$ .................... A01N 37/18; A01N 25/22
[52] U.S. Cl. .................................. 71/118; 71/DIG. 1
[58] Field of Search ............................ 71/DIG. 1, 118

[56] References Cited

U.S. PATENT DOCUMENTS

| | | | |
|---|---|---|---|
| 3,157,486 | 11/1964 | Harrison et al. | 71/120 |
| 3,421,882 | 1/1969 | Ordas | 71/118 |
| 3,480,671 | 11/1969 | Tilles et al. | 71/118 |
| 3,718,455 | 2/1973 | Baker et al. | 71/118 |
| 3,948,636 | 4/1976 | Marks | 71/79 |
| 4,071,617 | 1/1978 | Graves et al. | 71/79 |

FOREIGN PATENT DOCUMENTS 659675   3/1963   Canada ................................. 71/DIG. 1
1285930  1/1962   France ................................. 71/DIG. 1

*Primary Examiner*—Glennon H. Hollrah
*Attorney, Agent, or Firm*—M. Henry Heines

[57] ABSTRACT

A novel aqueous flowable concentrate of the herbicide 2-(α-naphthoxy)-N,N-diethyl propionamide is disclosed, displaying superior storage stability and dispersion and handling characteristics. The concentrate consists essentially of, by weight of the total concentrate:

(a) from 10 to 60% of 2-(α-naphthoxy)-N,N-diethyl propionamide;
(b) from 0.1 to 2.0% of a smectite clay;
(c) from 1.0 to 10.0% of a water-soluble nonionic surfactant;
(d) from 0.5 to 5.0% of a water-soluble dispersant; and
(e) from 1.0 to 20.0% of a water-soluble freezing point depressant;

the balance being water; the solid components have an average particle size of from about 5 to about 15 microns.

12 Claims, No Drawings

2-(α-NAPHTHOXY)-N,N-DIETHYL PROPIONAMIDE AS AN AQUEOUS FLOWABLE CONCENTRATE

BACKGROUND OF THE INVENTION

This invention relates to novel herbicide formulations. In particular, this invention relates to novel aqueous flowable concentrates of the herbicide 2-(α-naphthoxy)-N,N-diethyl propionamide.

This herbicide, whose common name is "napropamide," and which is manufactured by Stauffer Chemical Company under the trademark DEVRINOL ®, has the following structural formula

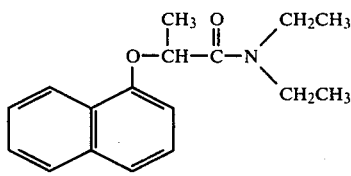

The synthesis and utility of this compound are disclosed in U.S. Pat. No. 3,480,671 (Tilles et al., Nov. 25, 1969), U.S. Pat. No. 3,718,455 (Baker et al., Feb. 22, 1973), and U.S. Pat. No. 3,998,880 (Mihailovski et al., Dec. 21, 1976).

Napropamide is a solid essentially insoluble in water and has been commercially available in the form of emulsifiable concentrates and wettable powders. The former is a solution of the herbicide and a surface-active compound in a water-immiscible or partially water-miscible solvent. When diluted with water, the solution forms an emulsion which is stabilized by the surface-active compound. Typical solvents for emulsifiable concentrates include mineral oils, petroleum products, chlorinated hydrocarbons, ethers, esters, and ketones. Unfortunately, a large amount of solvent is required, contributing substantially to the cost of the emulsifiable concentrate and accelerating the depletion of the natural resources from which the solvent was derived.

Wettable powders are water-dispersible powders containing the herbicide, an inert solid filler, and one or more surface-active agents to enhance wetting and prevent heavy flocculation when suspended with water. Typical solid fillers include natural clays, talcs, diatomaceous earth, and synthetic mineral fillers derived from silica and silicate. Unfortunately, it is difficult for the user to avoid contact with wettable powders during handling and mixing due to the dusty nature of the powders.

Flowable formulations, on the other hand, require little or no organic solvent and offer a greatly reduced possibility of user contact. Flowables are concentrated suspensions of a solid pesticide in an aqueous system. Having the characteristics of a thick liquid, a flowable formulation can be poured from a container, pumped, or otherwise transferred as any other viscous liquid. When the user is ready to apply the herbicide, he merely dilutes the flowable with water to the desired concentration and applies it to the field.

The optimum flowable formulation is one which demonstrates little or no settling and yet has a viscosity low enough to permit mixing and handling with reasonable ease. The optimum flowable will also have little susceptibility to syneresis whereby a thin liquid separates from the rest of the mixture, or to grit formation caused by the aggregation of the solid herbicide particles, particularly upon freezing and subsequent thawing of the suspension.

While various solid pesticides have been formulated as aqueous flowable concentrates, commercial preparations of napropamide have been mostly limited to emulsifiable concentrates and wettable poweders. It is therefore an object of this invention to provide an aqueous flowable concentrate of 2-(α-naphthoxy)-N,N-diethyl propionamide with little tendency to settle, little susceptibility to syneresis, and favorable freeze-thaw characteristics.

It is a further object of this invention to provide an aqueous flowable concentrate of 2-(α-naphthoxy)-N,N-diethyl propionamide, which is substantially homogeneous and thixotropic, in which the solid particles are substantially non-flocculated and have little or no tendency to settle to a hard cake upon standing which cannot be readily redispersed with mild agitation, and which dispenses spontaneously upon dilution with water.

A still further object of this invention is to provide a method of controlling undesired vegetation by applying to the locus where control is desired an aqueous dispersion of an herbicidally effective amount of 2-(α-naphthoxy)-N,N-diethyl propionamide formed by diluting the aqueous flowable concentrate of the present invention with water.

Further objects will be apparent from the following description.

BRIEF DESCRIPTION OF THE INVENTION

The present invention resides in two major discoveries. The first is that different combinations of the ingredients used in conventional flowable formulations of other herbicides give rise to widely differing results when combined with napropamide. The second is that a particular combination of ingredients produces a flowable formulation of unexpectedly superior properties.

In particular, it has been discovered that a water-based flowable napropamide formulation of superior stability and rheological properties can be obtained by combining the following components in the proportions stated:

| Component | Amount in Weight % |
|---|---|
| napropamide [2-(α-naphthoxy)-N,N-diethyl propionamide] | 10–60, preferably 20–50 |
| smectite clay | 0.10–2.00, preferably 0.25–1.00 |
| nonionic surfactant | 1.0–10.0, preferably 1.0–5.0 |
| dispersant | 0.5–5.0, preferably 0.5–2.0 |
| freezing point depressant | 1.0–20.0, preferably 10.0–20.0 |
| water | balance |

The above components are combined to form a dispersion and then milled such that the average particle size of the solids ranges from about 5 to about 15 microns, preferably from about 5 to about 10 microns.

The formulation may also contain additional components for further improvements in its properties, for example: viscosity modifiers, deflocculating agents, thixotropy modifiers, and syneresis control agents. These are discussed in detail below.

DETAILED DESCRIPTION OF THE INVENTION

The smectite clays whch are useful in the present invention include both the naturally-occurring and the synthetic smectities. The term "smectite" is commonly used to denote a group of expanding clays which are derived from pyrophyllites and talc by substitution of various metallic atoms in the clay structure. Specifically, the term "smectite" refers to minerals in the lower substitution ranges, to distinguish from the higher charge vermiculites. Examples of smectite clays are montmorillonite, beidellite, nontronite, saponite, hectorite, sauconite, stevensite, and bentonite. Many of these clays can be prepared synthetically by either a pneumolytic or hydrothermal synthesis. The preferred technique is the hydrothermal synthesis, in which hydrous oxides or hydroxides of the desired metals are placed in an aqueous slurry with sodium fluoride in proportions corresponding to those of the desired product. The slurry is then heated in an autoclave under autogenous pressure to 100° to 325° C. until a product of the desired composition is formed. Further discussion and descriptions of smectites may be found in "Rock Forming Minerals," Vol. 3, Sheet Silicates, by W. A. Deer et al., London 1962, pp. 226–245.

The nonionic surfactant of the present formulation serves primarily as a wetting agent. Suitable nonionic surfactants include all such water-soluble substances known to those skilled in the formulations art. Examples include long-chain alkyl and mercaptan polyalkoxy alcohols, alkylaryl polyalkoxy alcohols, sorbitan fatty esters, polyoxyethylene ethers, polyoxyethylene glycol esters, and polyoxyethylene esters of fatty and resin acids, as well as mixtures of the above. Preferred surfactants are the polyalkoxy alcohols.

The dispersant used in the present formulation can be any of the water-soluble materials well known to act as dispersants for finely divided solids in water. Examples of such materials are low-viscosity methyl cellulose, watersoluble low-viscosity partially hydrolyzed polyvinyl alcohol, polyoxyethylene sorbitan esters of mixed fatty acid rosin acids, purified sodium lignin sulfonates, sodium salts of polymerized alkaryl and aryl alkyl sulfonic acids, methyl hydroxyethyl cellulose, and carboxymethyl cellulose. Preferred dispersants are the sodium lignin sulfonates.

The freezing point depressant can be antifreeze or any other water-soluble substance which serves to lower the freezing point of water to an extent proportional to its molar concentration. Examples are low molecular weight glycols and alcohols such as ethylene glycol, propylene glycol, methanol, and isopropanol; ureas; and salts such as alkali and alkaline earth halides. The glycols are preferred.

Additional components can be included in the formulation at the option of the manufacturer or user. For example, xanthan gums, polymethylvinyl ether/maleic anhydride mixtures, carboxy vinyl polymers, and nonylphenoxy polymers are useful as thickening agents; sodium mono- and dimethyl naphthalene sulfonates and the like are useful for raising the thixotropic index; and pregelatinized starch and other polymers serve to decrease the occurrence of syneresis. The need for any of these additives will depend on the tendency of the dispersion to settle and on its susceptibility to handling, which in turn are determined by the relative quantities of each of the basic six ingredients: napropamide, the clay, the surfactant, the dispersant, the antifreeze, and water.

The napropamide is preferably milled in a hammermill or airmill to a particle size ranging from about 30 microns to about 5 millimeters in diameter prior to being combined in a pre-slurry with the other components of the formulation. Once the pre-slurry is formed, it is then further milled to reduce the solid particle size to the desired range of about 5 to about 15, preferably about 5 to about 10 microns. Ball mills, media mills, and colloid mills are examples of means effective for this final size reduction.

The invention is further illustrated by the following examples, which are intended neither to define nor limit the invention in any manner.

EXAMPLE 1

The following components were combined in the order and amounts given (totaling 400 g of formulation):

1. Geopon ™ GA-2, a purified smectite clay of particle size less than 1 micron, in aqueous dispersion at 4% by weight, obtained from NL Industries, Industrial Chemicals Division, Hightstown, N.J.—50.00 g, or 12.50 weight % of dispersion (0.50 weight % of clay)
2. Water—80.92 g, or 20.23 weight %
3. Ethylene glycol—60.00 g, or 15.00 weight %
4. Pluraflo ™ E4, a water-soluble, liquid, nonionic surfactant, characterized as a polyoxyethylene-polyoxypropylene copolymer, obtained from BASF Wyandotte Corporation, Wyandotte, Mich.—14.00 g, or 3.50 weight %.
5. Antifoam A, a silicone oil consisting of a dimethyl poly-siloxane and filler obtained from Dow Chemical Company, Midland, Mich.—0.40 g, or 0.10 weight %
6. Polyfon ™ H, a purified sodium lignin sulfonate dispersing agent, obtained from West Virginia Pulp and Paper Co.—4.00 g, or 1.00 weight %
7. Technical 2-($\alpha$-naphthoxy)-N,N-diethyl propionamide, 96% pure, milled by hammermill—190.68 g, or 47.67 weight %.

The seventh component was added to the first six slowly with mixing provided simultaneously by a high-speed Cowles blade. Once the addition was complete, the resulting flowable concentrate with particle size ranging from 1 to 16 microns, and an average particle size of 5 microns, as measured by an electrical resistance method on a Coulter Counter.

The concentrate was diluted with water and displayed spontaneous dispersion in the added water. A sample of the concentrate was cooled to −12° C. for three hours and remained fluid throughout. A further sample was frozen, solid in an acetone bath at −40° C. Upon subsequent thawing, the sample appeared smooth and homogeneous, i.e., no grits (aggregated napropamide particles) were observed. The thawed sample was then frozen and thawed three more times at −15° C. to −20° C., after which it still remained smooth and homogeneous.

Two additional samples were stored undisturbed for thirty days, one at ambient temperature and the second at 43° C. The freeze-thaw sample of the preceding paragraph was also stored for the same time period. At the end of the storage period, all three samples showed a slight degree of syneresis but no sediment formation.

Homogeneity was readily restored by shaking the sample container slightly.

EXAMPLE 2

The following components were combined in the amounts given (totaling 430 g of formulation):

Liquid components:
   water—210 g, or 48.89% by weight, propylene glycol—12 g, or 2.79% by weight,
   Pluraflo E4—14 g, or 3.26% by weight,
   Polyfon H—4g, or 0.93% by weight.

Solid components:
   Geopon GA-2 in dry form—2 g, or 0.47% by weight
   technical 2-(α-naphthoxy)-N,N-diethyl propionamide, 94% pure, hammermilled and airmilled—188 g, or 43.72% by weight This formulation differs from that of Example 1 by the substitution of propylene glycol for ethylene glycol, the elimination of the anti-foaming agent, and the use of dry smectite clay, as well as a lower concentration of napropamide.

The solid components were added to the liquid components and the resulting slurry was ball-milled down to an average particle size of 10 microns.

Upon dilution with water, the concentrate displayed spontaneous dispersion. A sample of the concentrate was frozen and thawed three times in succession, in the same manner as that described in Example 1, and the result was a smooth and homogeneous dispersion, with no grit formation.

A further sample was heated to 43° C. for 6 hours, showing no change in appearance. A still further sample was stored undisturbed at ambient temperature for 7 days, at the end of which time a slight degree of syneresis and sediment formation was observed, both of which were easily eliminated with slight manual shaking.

COMPARATIVE EXAMPLE 1

In this example, an attapulgus-type clay is used in place of a smectite-clay. The result is a flowable concentrate of substantially less stability, as the following description shows:

The following ingredients were used (total weight of formulation: 400 g):

Attagel TM 40, a specially processed form of the mineral attapulgite, obtained from Engelhard Minerals and Chemicals—2.0 g, 0.5 weight %
Water—190.6 g, 47.65 weight %
Propylene glycol—12.0 g, 3.0 weight %
Pluraflo E4—14.0 g, 3.5 weight %
Antifoam A—0.4 g, 0.1 weight %
Lomar TM PWA, a dispersant characterized as an ammonium salt of mononaphthalenesulfonic acid, obtained from Diamond Shamrock Chemical Co., Nopco Division, Morristown, N.J.—4.0 g, 1.0 weight %
Carbopol TM 941, a viscosity modifier characterized as a polyacrylic acid polymer, obtained from B. F. Goodrich Company—1.0 g, 0.25 weight %
technical 2-(α-naphthoxy)-N,N-diethyl propionamide, 94% pure, milled by hammermill and airmill—176.0 g, 44.0 weight %

The ingredients were combined in a slurry which was milled in a ball mill for six hours. The result was a dispersion with a pasty consistency. An additional 8 g of Lomar PWA and 8 g of Polyfon H were then added, together with additional water. The dispersion was now of a much more fluid nature and it was milled in a ball mill overnight.

The resulting dispersion had an average particle size of 7.2 microns and showed no sedimentation upon standing. After one freeze/thaw cycle, however, a sample of the dispersion became gritty, i.e., napropamide particles had aggregated. When heated to 43° C., sedimentation occurred.

COMPARATIVE EXAMPLE 2

In this example, an anionic surfactant is used in place of a nonionic surfactant as a wetting agent. As in Comparative Example 1, the result is a flowable concentrate with lesser stability, particularly upon freezing.

The following ingredients were combined in the order and amounts given (total weight of formulation: 400 g):

1. Geopon GA-2, as a 2% aqueous dispersion—100 g, 25.0 weight % of dispersion, 0.50 weight % of clay
2. Propylene glycol—12.0 g, 3.0 weight %
3. Nuosperse TM HOH, a dispersant characterized as an anionic water-soluble polymer, obtained from Tenneco Chemicals, Piscataway, N.J.—10 g, 2.5 weight %
4. Water—100.6 g, 25.15 weight %
5. Antifoam A—0.4 g, 0.1 weight %

To this mixture was added a second mixture consisting of the following:

technical 2-(α-naphthoxy)-N,N-diethyl propionamide—168 g, 42.0 weight %
Sellogen TM HR, an anionic surfactant used as a wetting agent, characterized as a sodium dialkylnaphthalene sulfonate, obtained from Diamond Shamrock Chemical Co., Napco Division—1.0 g, 0.25 weight %
Lomar PWA—4.0 g, 1.0 weight %

Finally, 4.0 g (1.0 weight %) of Polyfon H was added.

The slurry was milled for about six hours to produce a dispersion which dispersed readily and spontaneously when diluted with water. After two freeze-thaw cycles, however, grits appeared in the dispersion.

Clearly, the formulations within the scope of the present invention are more stable with regard to sedimentation and grit formation upon freezing and thawing.

EXAMPLE 3—HERBICIDAL ACTIVITY

To demonstrate the herbicidal activity of the formulations of the present invention, the formulation prepared in Example 1 was evaluated in a pre-plant soil incorporation test as follows:

Approximately four pounds of sandy loam soil with a moisture content of about 9% and containing 75 parts per million (ppm) of cis-N-[(trichloromethyl)thio]-4-cyclohexene-1,2-dicarboximide (a commercial fungicide bearing the name Captan ®) and 50 ppm of 18—1-8—18 fertilizer were placed in a 5-gallon (19-liter) rotary mixer. While the mixture was rotating, a 5milliliter sample of an aqueous dilution of the formulation of Example 1 was added. The dilution was prepared such that the treated soil contained a quantity of napropamide equivalent to 0.75 pound per acre (0.84 kilogram per hectare) when placed in a planting flat. Additional soil samples were treated in a similar manner using two current commercial formulations of napropamide—an emulsifiable concentrate and a wettable powder—for comparison testing in separate flats. The emulsifiable concentrate contained 2 lb active ingredient per gallon (0.24 kilograms per liter), and the wettable powder contained 50% active ingredient by weight.

Having thus been treated and mixed, the soil was placed in a 6-inch (15.2 cm) by 9-inch (22.9 cm) by 2.75-inch (7.0 cm) fiber planting flat. An amount of soil equivalent to a depth of 0.5-inch (1.3 cm) was removed and seven rows were impressed across the width of the flat. Each row was seeded with a single weed species. Ample seeds were planted to produce about 20 to 50 seedlings per row, the actual number in each row depending on the size of the plants in an untreated flat at the rating time. The seeds were then covered with the soil previously removed and the flats were placed in a greenhouse where they were watered daily and maintained at a temperature of 70°–85° F. (21°–29° C.).

The following weed species were used:

| Common Name | Scientific Name |
| --- | --- |
| barley | *Hordeum vulgare* |
| foxtail | *Setaria sp.* |
| watergrass | *Echinochloa crusgalli* |
| wild oat | *Avena fatua* |
| curly dock | *Rumex crispus* |
| annual ryegrass | *Lolium multiflorum* |
| johnsongrass | *Sorghum halepense* |

Three weeks after treatment, the degree of control was estimated by a visual comparison of treated flats with untreated flats. The degree of control in the treated flats was expressed as a percentage, using the untreated flats as a reference. Thus, for a given weed 0% represents no injury (i.e., growth comparable to that in an untreated flat) and 100% represents complete kill of the entire row. The results are shown in the table below.

| | Percent Weed Control Obtained With Napropamide at 0.75 lb/A | | | | | | |
| --- | --- | --- | --- | --- | --- | --- | --- |
| Formulation | Barley | Foxtail | Watergrass | Wild Oat | Curly dock | Rye | Johnsongrass |
| Flowable (Example 1) | 70 | 100 | 98 | 95 | 100 | 100 | 50 |
| Emulsifiable Concentrate | 50 | 95 | 95 | 80 | 100 | 90 | 30 |
| Wettable Powder | 75 | 98 | 98 | 90 | 100 | 100 | 40 |

These figures show that the results obtained with the new flowable formulation are equivalent if not better than those obtained with the commonly used emulsifiable concentrate and wettable powder.

As used herein, the term "herbicide" denotes a compound which controls or modifies the growth of plants. The term "herbicidally effective amount" is used to indicate any quantity of such a compound or a formulation of such a compound which is capable of producing such an effect. Controlling or modifying effects include all deviations from natural development, for example: killing, retardation, defoliation, desiccation, regulation, stunting, tillering, stimulating, leaf burn, dwarfing and the like. The term "plants" is intended to include germinating seeds, emerging seedlings, and established vegetation, including roots and above-ground portions.

The present flowable concentrate is diluted with water prior to application to the field. The dilution is conveniently done at the field site in a tank where agitation is provided to hasten the dispersion of the concentrate and to ensure a homogeneous mixture. The degree of dilution will be selected by the operator, whose decision will be based on the particular weeds to be controlled and the degree of control desired. Generally, sufficient water will be added such that the final dispersion will contain from about 0.01 to about 5.0 kilograms napropamide per liter of dispersion, preferably from about 0.1 to about 1.0 kilograms per liter.

Field application can be accomplished by any conventional technique designed for applying liquids. Spray techniques are particularly useful, ranging from boom sprayers, and hand sprayers to airplane sprayers. The locus of application can be soil, seeds, seedlings, or the actual plants, as well as flooded fields. Field application can also be accomplished by addition of the flowable concentrate or a diluted dispersion to irrigation water immediately before or while the latter is being supplied to the field. The application rate will be determined by the same factors mentioned in the preceding paragraph, and generally ranges from about 10 to about 1000 liters per hectare, preferably from about 50 to about 500 liters per hectare.

What is claimed is:

1. A flowable, storage-stable, aqueous pesticidal concentrate readily dilutable in water to form a spontaneous dispersion, which consists essentially of, by weight of the total concentrate,
    (a) from 10 to 60% of 2-(α-naphthoxy)-N,N-diethyl propionamide;
    (b) from 0.1 to 2.0% of a smectite clay;
    (c) from 1.0 to 10.0% of a water-soluble nonionic surfactant;
    (d) from 0.5 to 5.0% of a water-soluble dispersant; and
    (e) from 1.0 to 20.0% of a water-soluble freezing point depressant;
the balance being water; the solid components having an average particle size of from about 5 to about 15 microns.

2. A concentrate according to claim 1 consisting essentially of, by weight of the total concentrate,
    (a) from 20 to 50% of 2-(α-naphthoxy)-N,N-diethyl propionamide;
    (b) from 0.25 to 1.0% of a smectite clay;
    (c) from 1.0 to 5.0% of a water-soluble nonionic surfactant;
    (d) from 0.5 to 2.0% of a water-soluble dispersant; and
    (e) from 10.0 to 20.0% of a water-soluble freezing point depressant.

3. A concentrate according to claim 1 in which the solid components have an average particle size of from about 5 to about 10 microns.

4. A concentrate according to claims 1, 2, or 3, in which the nonionic surfactant is a polyalkoxy alcohol.

5. A concentrate according to claims 1, 2, or 3, in which the dispersant is a sodium lignin sulfonate.

6. A concentrate according to claims 1, 2, or 3, in which the freezing point depressant is a glycol.

7. A method of controlling undesirable vegetation which comprises applying to the locus where control is desired an herbicidally effective amount of a flowable aqueous concentrate consisting essentially of, by weight of the total concentrate,
    (a) from 10 to 60% of 2-(α-naphthoxy)-N,N-diethyl propionamide;
    (b) from 0.1 to 2.0% of a smectite clay;

(c) from 1.0 to 10.0% of a water-soluble nonionic surfactant;

(d) from 0.5 to 5.0% of a water-soluble dispersant; and (e) from 1.0 to 20.0% of a water-soluble freezing point depressant;

the balance being water; the solid components having an average particle size of from about 5 to about 10 microns.

8. A method according to claim 7 consisting essentially of, by weight of the total concentrate, (a) from 20 to 50% of 2-(α-naphthoxy)-N,N-diethyl propionamide;

(b) from 0.25 to 1.0% of a smectite clay;

(c) from 1.0 to 5.0% of a water-soluble nonionic surfactant;

(d) from 0.5 to 2.0% of a water-soluble dispersant; and (e) from 10.0 to 20.0% of a water-soluble freezing point depressant.

9. A method according to claim 7 in which the solid components have an average particle size of from about 5 to about 10 microns.

10. A method according to claims 7, 8, or 9 in which the nonionic surfactant is a polyalkoxy alcohol.

11. A method according to claims 7, 8, or 9 in which the dispersant is a sodium lignin sulfonate.

12. A method according to claims 7, 8, or 9 in which the freezing point depressant is a glycol.

* * * * *

UNITED STATES PATENT AND TRADEMARK OFFICE
CERTIFICATE OF CORRECTION

PATENT NO. : 4,266,965
DATED : May 12, 1981
INVENTOR(S) : Richard W. Simons

It is certified that error appears in the above-identified patent and that said Letters Patent are hereby corrected as shown below:

In Column 4, at line 48, after the word "resulting" please insert the following —

" slurry was ball-milled for 17 hours. The result was a "

Signed and Sealed this

Twenty-ninth Day of September 1981

[SEAL]

Attest:

GERALD J. MOSSINGHOFF

Attesting Officer

Commissioner of Patents and Trademarks